United States Patent [19]
Chang et al.

[11] Patent Number: 4,841,967
[45] Date of Patent: Jun. 27, 1989

[54] POSITIONING DEVICE FOR PERCUTANEOUS NEEDLE INSERTION

[76] Inventors: Ming Z. Chang, 8 Flynn Ter., West Orange, N.J. 07052; Chuen M. Yeh; Chuen Y. Yeh, both of 15 Stratford Cir., Edison, N.J. 08820

[21] Appl. No.: 575,017

[22] Filed: Jan. 30, 1984

[51] Int. Cl.[4] .............................................. A61B 19/00
[52] U.S. Cl. .................................................. 128/303 B
[58] Field of Search ............... 128/305, 303 B, 303.19, 128/791, 784, 644, 642

[56] References Cited

U.S. PATENT DOCUMENTS

| | | | |
|---|---|---|---|
| 1,093,112 | 4/1914 | Clarke | 128/303 B |
| 1,129,333 | 2/1915 | Clarke | 128/303 B |
| 3,115,140 | 12/1963 | Volkman | 128/303 B |
| 3,135,263 | 7/1964 | Connelly, Jr. | |
| 3,196,875 | 7/1965 | Pfeiffer | 128/303 B |
| 3,384,086 | 5/1968 | Rocha-Miranda et al. | 128/305 |
| 3,542,030 | 11/1970 | Hoffman et al. | 128/303 B |
| 3,817,249 | 6/1974 | Nicholson | 128/303 B |
| 4,230,117 | 10/1980 | Anrchkov | 128/303 B |
| 4,294,119 | 10/1981 | Soldner | |
| 4,350,159 | 9/1982 | Gouda | 128/303 B |
| 4,386,602 | 6/1983 | Sheldon et al. | 128/303 B |

FOREIGN PATENT DOCUMENTS

| | | | |
|---|---|---|---|
| 2115121 | 10/1972 | Fed. Rep. of Germany | 128/303 B |
| 179419 | 7/1966 | U.S.S.R. | 128/303 B |
| 441933 | 12/1974 | U.S.S.R. | 128/303 B |
| 764670 | 9/1980 | U.S.S.R. | 128/303 B |
| 818711 | 8/1959 | United Kingdom | 128/303 B |

OTHER PUBLICATIONS

"Interventional Radiology of the Abdomen", Joseph T. Ferrucci et al., pp. 124–135 (1981).
"Interventional Radiology", Athanasoulis, et al., pp. 561–583 (1982).
M. P. Heilbrun et al., J. Neurosurg., vol. 59, pp. 217–222 (1983).

Primary Examiner—Robert P. Swiatek
Assistant Examiner—J. Hakomaki
Attorney, Agent, or Firm—Jack B. Murray, Jr.

[57] ABSTRACT

This invention is directed to a device for accurately positioning needles for percutaneous insertion which comprises the elements of a base having a vertically disposed support member at one end thereof, a plate rotator, a needle holder, a tilt angle adjuster for the needle holder, and an arcuate needle angle indicator.

In a second embodiment, the needle holder further comprises a circular angle indicator which includes a circular angular tilt angle of the needle holder to be observed by reference to the circular disk.

7 Claims, 4 Drawing Sheets

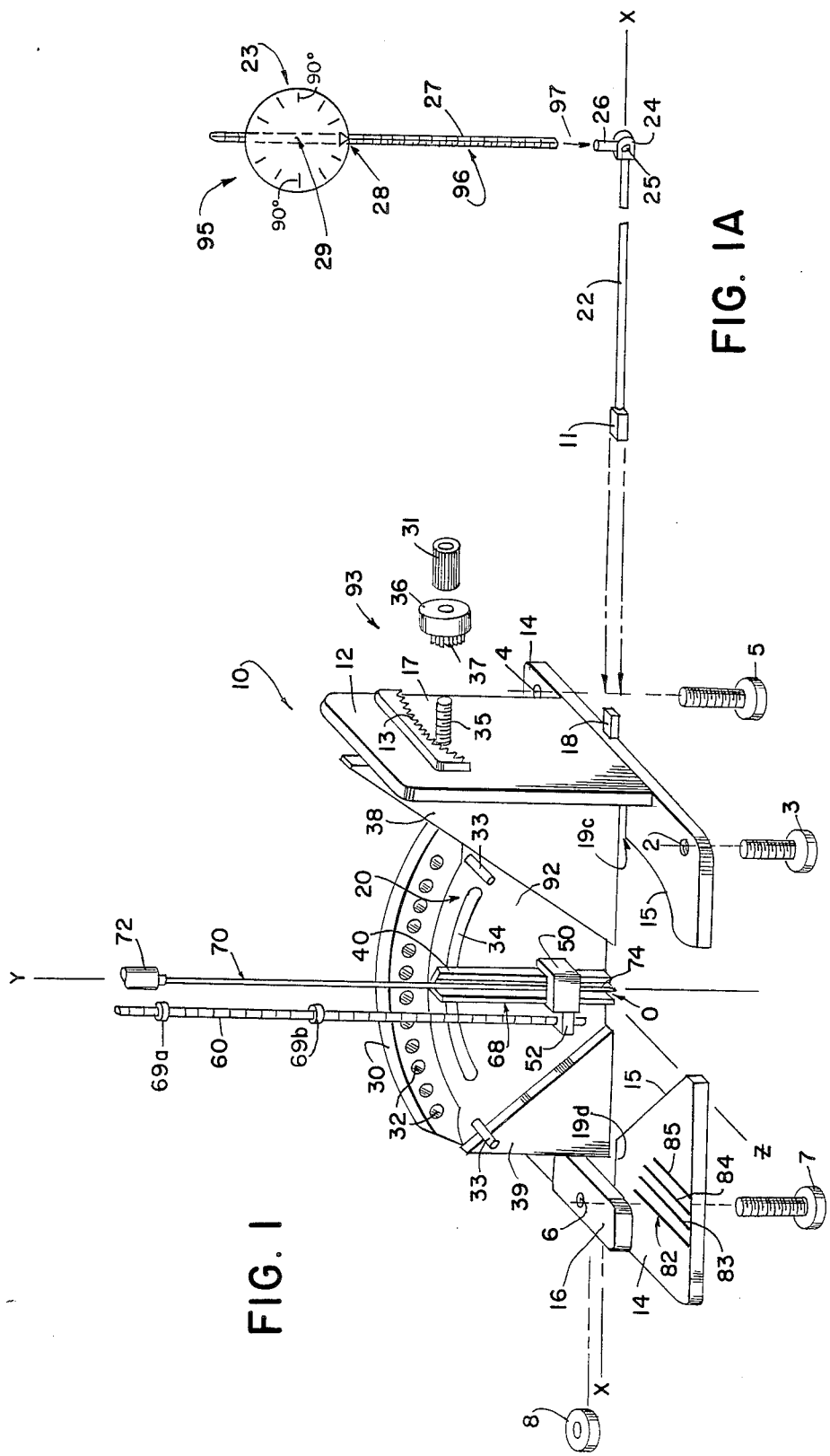

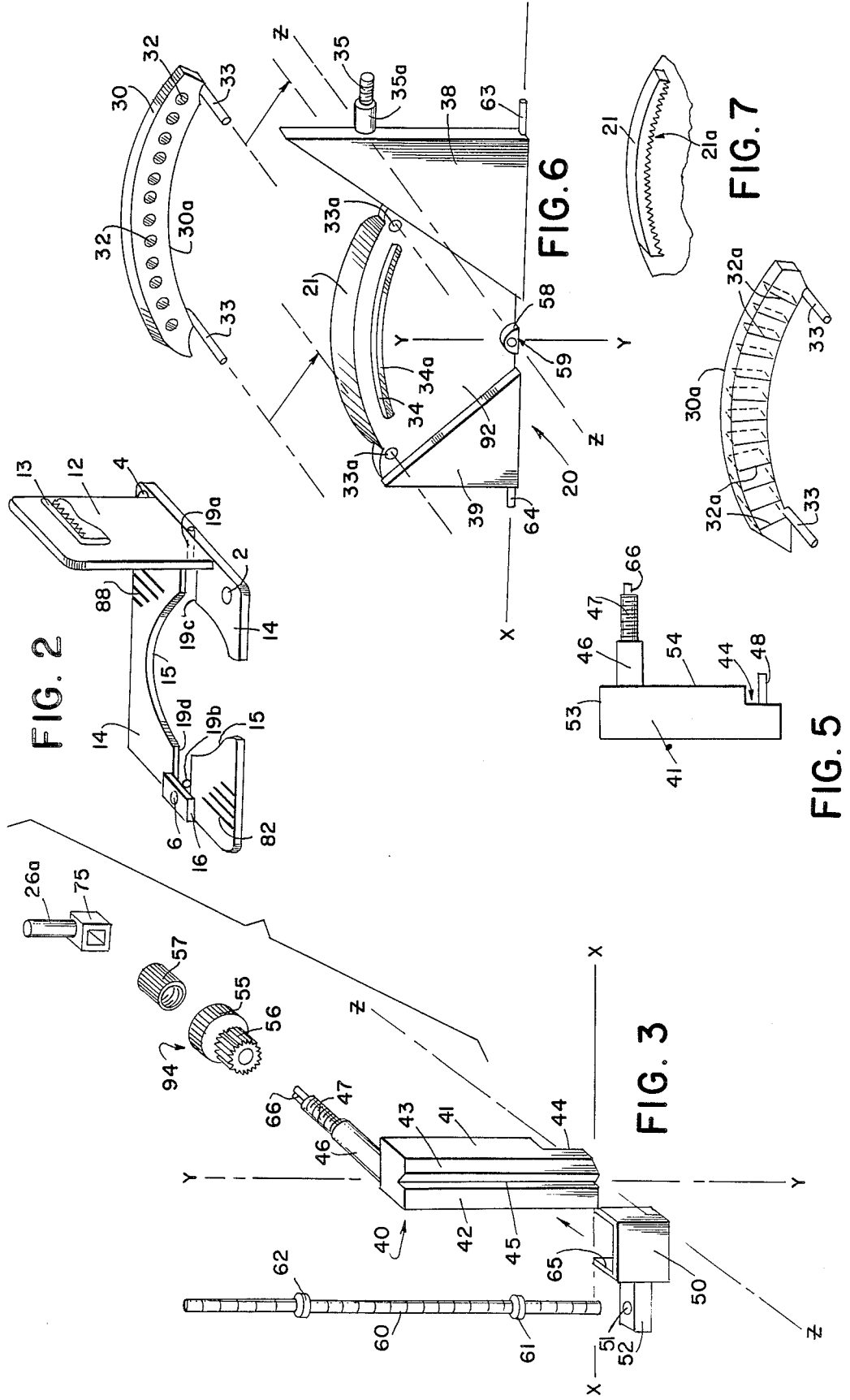

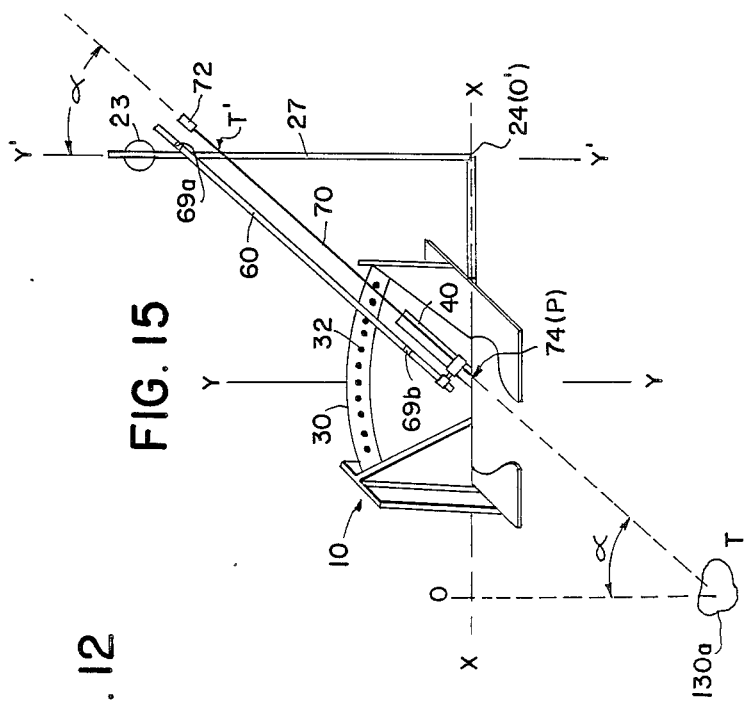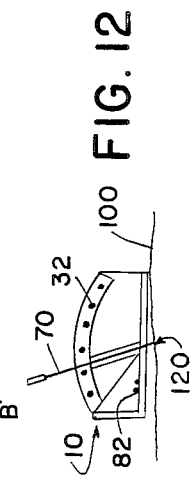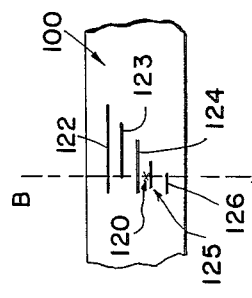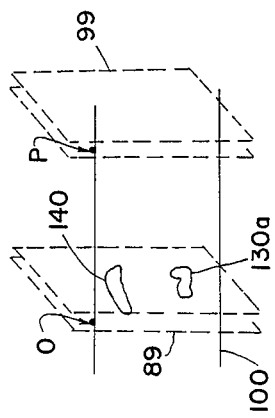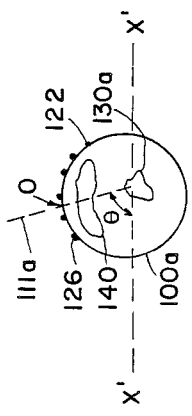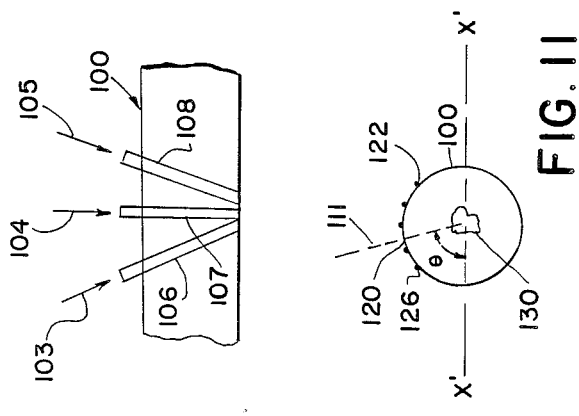

POSITIONING DEVICE FOR PERCUTANEOUS NEEDLE INSERTION

BACKGROUND OF THE INVENTION

1. Field of the Invention

This invention relates generally to devices for positioning of medical instruments such as needles for accurate percutaneous insertion, and more particularly to devices for such positioning of needles and other medical instruments in combination with X-ray emissions.

2. Description of the Prior Art

The conventionally and widely used "CAT Scan" device, a computer controlled X-ray instrument which can provide cross-sectional imaging of body tissues, is a very powerful modern instrument which has a wide range of uses. One such use is the precise location of body tissues which are desired to be accessed, as by use of long, thin needles or other medical instruments (such as catheters) by percutaneous insertion, for taking biopsy samples of such target tissues or for further medical treatment (such as draining abcesses or removing foreign bodies therefrom).

However, currently trial and error methods are used to insert such needles and medical instruments in response to the cross-sectional images generated by the CAT Scan device, in order to puncture the skin and reach the desired target point. This can result in repeated puncturing of the skin which carries with it the enhanced risk of damage to body organs adjacent to the target point lying along the path which the needle is desired to travel. Moreover, many target points may lie too close to vital nerve or other body tissues, or no safe path may be available to permit the needle to circumvent vital body organs lying along the desired puncture path. In such cases, the risk to the patient in reaching the target point may be so great as to prevent the use of, e.g. needle biopsy, and further medical diagnosis and treatment might then require exploratory surgery. This of course entails significant trauma, expense, time and manpower in conducting the surgery, and also entails added post-operative time and expense.

Heretofore, no device or method has ben found which alleviates the need for subjecting the patient to such trial and error needle positioning. Prior art trial and error methods of acomplishing percutaneous tumor biopsy and absecess drainage, and the risks associated therewith, are discussed in "Interventional Radiology of the Abdomen", Joseph T. Ferruci, et al., pp. 124–135 (Williams and Wilkins 1981); "Interventional Radiology", Athanasoulis, et al., PP. 561–583 (W. B. Saunders Co. 1982); and M. P. Heilbrun, et al., "Preliminary experience with Brown-Roberts-Wells (BRW) computerized tomography stereotaxic guidance system", *J. Neurosurg.* vol. 59, pp. 217–222 (1983), the disclosures of which are hereby incorporated by reference.

Devices which have been developed for cranial surgery and treatment include those disclosed in U.S. Pat. Nos. 3,115,140; 3,135,263; 4,294,119; and 4,350,159, and in Russian Patents 441,933 and 764,670. However, these devices are complex and cumbersome, and are not readily adaptable for use on body parts other than the head.

SUMMARY OF THE INVENTION

A device is provided which is useful in accurately positioning needles and other thin, elongated medical instruments intended for percutataneous insertion through the skin to a predetermined target within the body of a patient. The device comprises (i) a base, provided at one end thereof with a vertically disposed support member, (ii) turning plate means movably affixed to the base and adapted to be tilted in a direction which is substantially parallel to the plane defined by the vertical support member, (iii) means for adjusting the tilt angle of the turning plate means; (iv) needle holding means, movably affixed to the turning plate means, for removably securing a needle or other elongated medical instrument thereto and adapted to be tilted along the turning plate in a plane which is substantially perpendicular to the plane defined by the vertical support member (v) means for adjusting the tilt angle of the needle holding means; and (vi) arcuate needle angle indicator means, provided with a plurality of spaced-apart radiopaque needle angle indicators along the upper periphery of the arcuate turning plate means and adapted to provide a visible indication of the needle tilt angle along the turning plate means when the device is exposed to X-ray emissions, the balance of said device being constructed of a material which is substantially transluscent to such radiation.

The needle holding means can further comprise a needle depth measuring means for indicating the depth to which the needle is to be inserted into the body cavity, and the base can further comprise screw threaded height adjusting means for adjusting the height of the base avobe the skin and for leveling the device thereon. The needle holding means can also be provided with a longitudinal, vertically disposed radiopaque indicator line to aid in determining the needle tilt angle.

The device of this invention can further comprise a circular angular indicator means, adapted to be removably attached to the turning plate means and needle holding means such that the tilt angle of the turning plate means and needle holding means can be accurately determined by means of a rotatable circular angle indicator disk.

BRIEF DESCRIPTION OF THE DRAWINGS

FIGS. 1–1A are perspective elevational views of an embodiment of the device of this invention provided with an offset angle indicator means.

FIG. 2 is a perspective, elevational view of the base of FIG. 1.

FIG. 3 is an exploded, perspective view in elevation of the needle holding means and an associated turning nut and locking nut for positioning the needle holder, circular angle indicator adaptor and elongated depth gauge of the device illustrated in FIG. 1.

FIG. 5 is a side elevational view of the needle holder illustrated in FIG. 3.

FIG. 6 is an exploded view, in perspective and elevation, of the turning plate of FIG. 1 and an associated radiopaque arcuate angle indicator.

FIG. 7 is an elevational view of a portion of the reverse face of turning plate of FIG. 6 and illustrates the gear rail thereof.

FIG. 8 is a perspective elevational view of another embodiment of the arcuate needle angle indicator.

FIG. 9 is a simplified cross-section of a body part.

FIG. 10 is a simplified top view of the body part of FIG. 9 with radiopaque skin markers thereon.

FIG. 11 is a cross-sectional view of the body part of FIG. 10 taken along line B—B', slightly rotated.

FIG. 12 is a simplified elevational view of a device 10 of FIG. 1 positioned above puncture point 120 on the sking of body part 100.

FIG. 13 is a cross-sectional body part view as in FIG. 11 except that a body organ 140 lies on the needle pathway.

FIG. 14 is a simplified, perspective view of a body part as in FIG. 13 showing a vital organ and target.

FIG. 15 is a simplified perspective view of a device 10 of this invention used in combination with an offset angle indicator means of this invention.

DETAILED DESCRIPTION OF THE PREFERRED EMBODIMENT

Figure 1B:
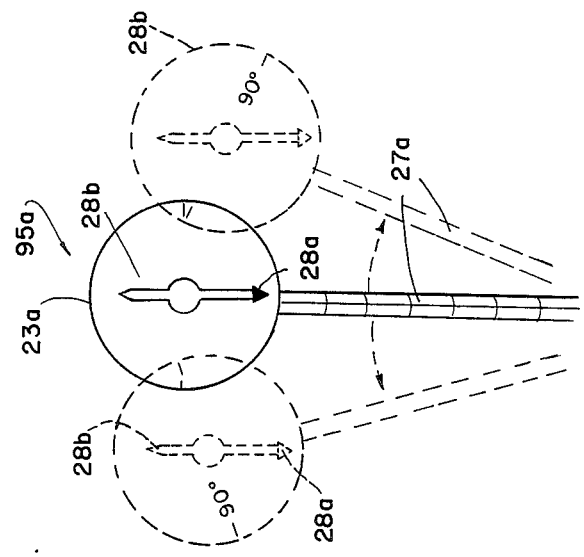
FIG. 1B is an elevational view of a second embodiment of an offset angle indicator means having a circular angle indicator disk.

Referring to FIGS. 1-7, one embodiment of the device of this invention is illustrated which comprises base 14, vertical support member 12, turning plate means 20, needle holder means, generally indicated at 68, and arcuate needle angle indicator means 30.

Vertical support member 12 is positioned along one side of base 14 and is provided with arcuate aperature 17 therethrough, and first arcuate gear rail 13 above arcuate aperature 17.

Turning plate means 20 comprises supporting, opposing triangular-shaped end portions 38 and 39, planar mid-portion 92. Turning plate turning means, indicated generally at 93, comprises cylindrical axle support 35a, screw threaded member 35, turning nut 36 and locking nut 31.

Turning plate 20 is movably affixed to base 14 by means of pins 63 and 64 which are affixed to the lower portion of each end of plate 20 (and can be integrally formed therewith) and are each rotatably housed in the associated pin cavities 19a and 19b in base 14, to permit turning plate 20 to be tilted in a direction which is parallel to the plane defined by vertical support member 12, namely, in the YY-ZZ plane. The substantially flat lower surface of plate 20 adjacent to pins 63 and 64 are movably positioned within channels 19c and 19d of base 14, which should each be of a sufficient width to permit plate 20 to turn, without binding the portions of base 14 surrounding cavities 19a and 19b.

At the upper portion of one side 38 of turning plate 20 is provided cylindrical axle support 35a and screw threaded member 35 which are adapted to be inserted through aperature 17 of vertical support member 12, and to be movably affixed to support 12 in a plurality of positions along the arcuate aperature 17 by means of locking nut 31 and turning nut 36. Locking nut 31 is provided with screw threads to engage the screw threaded member 35, and turning nut 36 is sized slightly larger than axle 35a to permit nut 36 to be turned, and engage the gear rail 13, without imparting rotational force to axle 35a, on which nut 36 is positioned. Therefore, it can be seen that axle support 35a should be of a length which is sufficient to enter aperature 17 and extend therebeyond to permit nut 36 to rest thereon. Nut 36 is provided with gears 37 which are adapted to mesh with gear rail 13. When so constructed, turning plate 20 can be tilted in a plane substantially parallel to the plane (YY-ZZ in FIG. 1) formed by vertical support member 12, and the tilt angle of plate 20 can be fixed and precisely adjusted by means of gears 37, gear rail 13 and locking nut 31. For example, when locking nut 31 is loosened slightly upon member 35, turning nut can then be rotated in the desired direction, whereupon gears 37 and gear rail 13 act to precisely adjust the tilt angle of plate 20. Nut 31 can then be again tightened to maintain the selected tilt angle of plate 20.

The total angular adjustment possible for plate 20 can be set by the length of aperature 17, and can vary widely, with a total of 160 degrees of angular tilt (that is, 80 degrees of tilt away from the vertical in either direction) will be generally sufficient for turning plate 20.

Needle holder means 68 comprises needle holder 40 and removable clasp 50. Needle holder 40 comprises a longitudinal grooved housing adapted to receive a needle 70 (or other elongated medical instrument intended for percutaneous insertion into a body cavity) in a longitudinal groove 45 defined in the front face 43 of housing 40. The needle 70 can be removably affixed to housing 40 by means of a removable clasp 50 which can be fabricated from a material and of a size such that the inner sides 65 of clasp 50 securely grip the sides 41 of housing 40 to hold needle 70 within groove 45 and to prevent needle 70 from moving, of its own weight, downwardly when holder 40 is positioned vertically, as in FIG. 1. The frictional resistance to such downward motion of needle 70 should not, however, be sufficient to prevent the needle 70 from being repositioned by application of external force, as by hand, to precisely adjust the position of needle tip 74 in use of the device of this invention, which is generally indicated at 10 in FIG. 1.

Clasp 50 can be provided with housing 52 extending outwardly therefrom and provided with aperature 51 to secure a longitudinal needle depth gauge 60 therein such that the shaft of gauge 60 extends upwardly from housing 52 and remains parallel to needle 70 throughout any adjustment of the needle tilt angle, as will be explained in more detail below.

Needle holder 40 is further provided with a recessed portion 44 in the lower portion of inner face 54 of housing 40, and a pin 48 is affixed to the inner recessed surface of face 54, preferably centrally in such recessed face. Pin 48 is adapted to be received by pivot cavity 59 in a pivot structure 58 which is provided centrally in the lower portion of turning plate 20.

At the upper portion of rear face 54 of housing 40 is affixed a cylindrical support axle 46 and screw threaded member 47 which are adapted to be inserted into arcuate aperature 34 in planar mid-portion 92 of turning plate 20, and to be movably affixed to turning plate 20 be means of needle holder turning means, indicated generally at 94, which comprises turning nut 55 and locking nut 57. Nut 57 is provided with screw threads to engage the screw threaded member 47, and turning nut is sized to rest upon axle 46 and is provided with gears 56 which are adapted to mesh with gear rail 21. Turning nut 55 is sized slightly larger than axle 46 to permit nut 55 to be turned without imparting rotational force to axle 46. Therefore, the needle tilt angle, which is adjusted by means of movement of needle holder 40 along turning plate 20, can be precisely adjusted in a manner similar to that described above for adjustment of the turning plate tilt angle itself. When so constructed, needle holder 40 can be moved independently of the angle selected for turning plate 20, with needle tilt angles being adjusted by means 94 along a planar direction which is parallel to the plane then formed by turning plate 20 (which is the XX-YY plane as illustrated in FIG. 1 when plate 20 is in the vertical position) and which is therefore perpendicular to the plane defined by vertical support member 12.

The total angular movement permitted for needle holder 40 can be determined by the length of aperature 34 and can vary widely, with a total of 160 degrees (that is, 80 degrees away from the vertical in either direction) being generally sufficient. It will therefore be seen that turning plate 20 and needle holder 40 can be independently positioned to result in a wide range of possible attitudes of needle 70, relative to the vertical YY axis.

Upon the upper surface 21 of turning plate 20 is positioned arcuate needle angle indicator plate 30 which is provided with a plurality of spaced-apart, radiopaque needle angle indicator marks 32 which are adapted to give a visual indication of the needle tilt angle of needle 70 when device 10 is exposed to either visible light and, more importantly, also to X-ray emissions such as are normally employed in CAT Scan devices of the prior art. Therefore, indicator marks 32 can be composed of any known radiopaque material such as barium sulfate, metal iodides, metal alloys and the like, and plate 30 can be formed from a plastic material, which contains marks 32 and is otherwise transparent or translucent to such X-ray emissions. Arcuate plate 30 can be either removably affixed to turning plate 20 (as shown in FIG. 1, as by means of pins 33 which are affixed to plate 30 and are adapted to be inserted into associated aperatures 33a in turning plate 20. Alternatively, arcuate plate 30 can be formed integrally with turning plate 20 (not shown).

Indicator marks 32 can comprise any convenient shape and can be used in any convenient number on plate 30. Generally, from about 10 to 50 such marks 32 will be sufficient. Each such mark 32 is preferably separated from its adjacent marks 32 by a distance which is sufficiently large to avoid blurring of two or more marks as a result of the resolution of the imaging device (e.g., X-ray sensitive photographic film) normally associated with prior art CAT Scan devices. Generally, a separation distance of from about 2 to 4 mm will be sufficient. Similarly, the shape of marks 32 is not critical, and they may be rounded (as in FIG. 1) or linear. FIG. 8 illustrates linear marks 32a, each of which can comprise the front face of a radiopaque flat plate extending through the width of the arcuate plate 30a. The precise dimensions of marks 32 necessary to achieve sufficient radiopacity to permit ready observation of needle angles using a conventional CAT Scan device will depend on such factors as the particular radiopaque material selected for use, the shape of marks 32 and other factors, and can be readily determined by one having ordinary skill in the art given the present disclosure. Furthermore, the balance of device 10 can be constructed of such known, substantially non-radiopaque materials as plastics (e.g. Lucite, polyethylene, polypropylene and the like) and other known such materials of construction.

Referring now to FIG. 1A, there is illustrated an offset angle indicator means, indicated generally at 95, which comprises shaft 22, connector 11, angularly adjustable connector 24, linear gauge 27 and circular angle indicator means 23, which is substantially transparent and is provided with an angular scale and a weight 28 affixed to the lowest portion of disk 23, which is rotatably affixed to gauge 27 by means of axle 29 to permit disk 23 to freely rotate such that weight 28 continues to point downwardly when linear gauge 27 is tilted from the vertical. Alternatively, the circular angular indicator can be fixed to linear gauge 27 and can be provided with a weighted, freely rotating pointer 28b, having a weight mass 28a at its lower end, so that pivoting pointer 28b will continue to point downwardly when gauge 27 (indicated as gauge 27a in FIG. 1B) is tilted from the vertical.

Gauge 27 is provided with distance scale markings thereon (e.g., mm) and is also provided with a center line 96, in the preferred embodiment. The lower portion of gauge 27 (indicated at 97 in FIG. 1A) is adapted to be removably secured to nub 26 of adjustable connector 24. Both gauge end portion 97 and nub 26 are each of a circular cross-section so that their rounded dimensions facilitate the movement and positioning of gauge 27 thereon. Alternatively, both end portion 97 and nub 96 can be formed to have a substantially rectangular (preferably square) cross section to permit accurate positioning of the plane of disk 23 relative to the plane defined by the shaft 22 and linear gauge 27 (that is, either parallel or perpendicular to the XX-YY plane as defined in FIG. 1). Connector 11 is adapted to be removably secured to a nub 18 which is provided at one side of base 14 along the X-X axis and affixed to the extending portion of pin 63 (which is affixed to plate 20) and mounted thereon so as to rotate in a direction and in response to the movement of turning plate 20 in adjusting plate 20 angle, as defined above. (Although not shown, it will be understood that pin 63 projects through base 14 sufficiently to permit nub 18 to be affixed thereto, as described.) A separate such nub (not shown) can be provided along the X-X axis on the opposite side of base 14 and similarly, rotatably affixed to pin 64 of turning plate 20. The angle of tilt of gauge 27 can be adjusted by loosening a thumb screw 25 to permit nub 26 to pivot in XX-YY plane (as shown in FIG. 1) to the desired angle, which can then be observed directly on the angular scale of circular indicator 23. The selected angle can be maintained by tightening thumb screw 25. The offset angle indicator means 95 of this invention can be employed with device 10 of this invention to permit percutaneous insertion of needle 70 to reach targets which are not otherwise accessible, as will be illustrated hereinafter.

Figure 4:
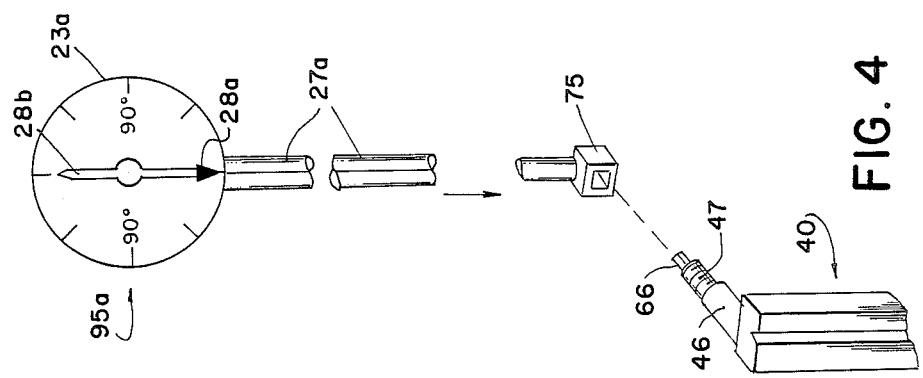
FIG. 4 is an exploded, elevational perspective view of the circular angle indicator and adaptor 75 to the needle holding means.

Referring to FIG. 4, it can be seen that a circular angle indicator 23 can also be employed to visually indicate, directly, the needle tilt angle of needle holder 40, by the provision of a suitable nub 66 at the end portion of screw threaded member 47 of holder 40. Nub 66 then acts to mate with a connector 75 which is provided another nub 26a, situate at right angle relationship to the center axis of screw threaded member 47, which is sized so as to mate in turn with lower end portion 97 of linear gauge 27 (or gauge 27a). By such means, the positioning of needle holder 40 along turning plate 20, as described above, will cause linear gauge 27 to move accordingly. Since gauge 27, when positioned upon nub 26a, will lie parallel to needle 70, the needle tilt angle can be read directly on circular disk 23 (or 23a, as the case might be).

The method of use of device 10 can be further understood by reference to FIGS. 9-12. Body part 100 (e.g., the abdomen) can be subjected to X-ray beams 103, 104 and 105, using conventional methods (which do not form a part of this invention), to generate cross-sectional images 106, 107 and 108, respectively, using a conventional CAT Scan device (which also forms no part of the present invention). Image 107 represents a vertical image plane, image 106 represents a cross-sectional image plane which is −20° from vertical, and image 108 represents a cross-sectional image plane which is +20° from vertical. After the desired image plane angle on the CAT Scan device is selected (which can generally range from −20 to +20 degrees from the vertical), radiopaque indicator lines 122-126 are marked (or taped) on the patient's skin of body part 100 above the general area of the target 130. An image is then made which identifies ouncture point 120 as lying midway between indicators 124 and 125 and which provides the required needle pathway 111, as shown in FIG. 11. The scanning plane can be visually projected on the skin by use of the internal alignment light beam which is a component of conventional CAT Scan devices. Device 10 can then be placed on the skin with point "O" of the needle holder located upon puncture point 120, and the axis X-X of device 10 superimposed with the scanning plane visually projected onto the skin (which can be marked thereon with a suitable ink, if desired). The tile angle of the turning plate 20 is then adjusted according to the circular angular indicator 23 attached to nub 18 as described above, such that plate 20 is secured (by turning means 93) at an angle which corresponds to the selected image plane angle (e.g., image plane 103, which is 3120 degrees from the vertical). If desired, the tilt angle of plate 20 can be precisely compared to the image plane angle by use of external alinment light beam, which are also generally provided on conventional CAT Scan devices and which comprise a thin beam of visible laser beam which is projected across the skin of body part 100 and coincides with the direction of the image plane which will result when the X-ray emissions of the CAT Scan device are activated to generate the desired image. The tilt angle of the needle holder 40 is then adjusted according to the angle "$\theta$" of the needle path 111 to the horizontal line X″—X′ in FIG. 11 (e.g., −80 degrees from the horizontal) which is provided by the CAT Scan device's image. An imaging scan can then be taken and the relationship between target point 130, puncture point 120 and device 10 accurately established, such that a line connecting points 120 and 130 can be extended to intersect with the arcuate plate 30, thereby permitting observation of the required needle tilt angle by means of radiopaque marks 32 which appear on the cross-sectional image thus obtained. The needle tilt angle can then be precisely adjusted by movement of the needler holder 40 as described above by operation of turning means 94. Then, the depth from skin puncture point 120 to target 130 can be ascertained from the image (as in FIG. 11), and the needle depth gauge 60 can be employed (by suitable positioning of slideable tabs 69a and 69b) to mark the corresponding depth. Therefore, tab 69a can be placed adjacent to a defined section of needle 70, for example, at the lower edge of shaft connector 72, which connects needle 70 to a conventional plunger (not shown), and tab 69b can then be placed below tab 69a at a distance which corresponds to the desired needle insertion depth. Needle 70 can then be inserted through the patient's skin at 120 along path 111 by operation of the plunger, to the predetermined depth marker 69a to reach target 130. If desired, base 14 can be taped to the skin for stability.

To permit the thus-inserted needle to be used for exchanging and insertion of other, larger elongated medical instruments along path 111, for the desired tissue sampling, observation or treatment, base 14 of device 10 is preferably provided with an enlarged center opening, as defined by walls 15 in the embodiment illustrated in FIG. 1, to permit device 10 from being removed from the patient's skin without disturbing (or requiring the removal of) the thus-positioned needle 70. Preferably, base 14 has a substantially discontinuous outer periphery along one side thereof, as shown in FIG. 1, adjacent to needle holder 40, to permit more fascile removal of device 10 after insertion of needle 70.

It has been found that the foregoing device 10 and above-described method permit accurate and rapid determination of needle path 111 and insertion of needle 70, and this invention has resulted in saving of as much as 75% or more of the time needed using prior art needle biopsy methods.

Referring again to FIGS. 1 and 2, radio opaque linear marks (e.g., 82–85 and 88) are provided on the upper surface of base 14 at diagonally opposing sides thereof. Each set of such marks (e.g., marks 82–85) should comprise at least 2 to 3 such marks in decreasing lengths, and the difference in length of each successive mark in a given set should be constant and equal to the distance by which the longest such mark (e.g., mark 82) in each set is separated from the center axis (X-X) of turning plate 20. In this manner, if the patient moves slightly after turning plate 20 is precisely aligned with the desired image angle, one or more dots will appear when the image is actually obtained, at one side of puncture point 120. The number and position of these dots (illustrated at 82 in FIG. 12) will indicate the direction and distance of the movement away from the planned image plane. For example, in the image taken in FIG. 12, if the constant length difference was 5 mm., then the appearance of two dots to the left of the puncture point 120 indicates that the patient has moved about 10 mm (and not more than about 14 mm) in a direction which is into the paper as viewing FIG. 12. Had these dots appeared on the opposite side of point 120, it could be concluded that the movement occurred in a direction which is out of the plane of the paper, toward the viewer, as viewing FIG. 12. In this manner, the scanning plane can be adjusted by moving the surface (generally a slidable table) on which the patient is positioned, in a direction and for a distance sufficient to compensate for this unexpected slight movement.

Referring to FIG. 13, there is illustrated a cross-sectional image scan of body part 100a showing a target body object 130a, vital body organ 140 and a plurality of linear radio opaque indicator skin markers (e. g., 122 and 126). Similarly to the scan shown in FIG. 11, a projected needle path 111a can be defined between puncture point "O" and target 130a. However, in this case a vital body organ 140 would be punctured if path 111a were followed. Use of an offset angle indicator 95 of this invention, in combination with a device 10, will now be described, having reference to FIGS. 14 and 15.

In the image scan of FIG. 13, shown in perspective as scan 89 in FIG. 14, body organ 140 lies in a direct line from desired puncture point "O" to target 130a. A second scan is taken, using the same image plane angle, which can be accomplished by conventional means, as by moving the patient linearly and maintaining the angle settings of the imagining device that were previously selected. The second scan image 99 results in a new puncture point "P", and it is seen that no vital organs lie in the path of P to 130a. A straight line is drawn on the patient's skin to connect O-P, and device 10, having offset indicator means attached thereto, is positioned above "P", with the needle point 74 being placed upon "P". The turning plate 20 is aligned with its X-X axis coinciding with the line formed by O-P. The tilt angle of the turning plate 20 is then adjusted, as is the tilt angle of the needle holder 40 as described above (e.g., according to an angle "θ" between line 111a and horizontal line X'—X' as shown in FIG. 13. The length of shaft 22 is chosen such that the distance from "P" to the center of connector 24 is equal to the length of line O-P. The circular indicator 23 is positioned (by means of selecting the relationship of nub 26 and lower end portion 97) such that the plane of indicator 23 is in the XX-YY plane. The angle of gauge shaft 27 is then adjusted as described above such that it corresponds to the angle of the image plane employed to obtain the scans 89 and 99 (which is assumed to have been vertical in FIGS. 14 and 15). Since O-T, the depth from "O" to the target 130a is known from scan 89, the same distance from X-X axis along gauge 27 can be measured, and point T' marked thereon. The needle tilt angle O'PT' along turning plate 20 can then be readily adjusted, by moving needle holder 40 until needle shaft 70 intersects point "T'" on shaft 27. Since line O-P equals P-O', and O-T equals O'-T', it can be seen that the puncture distance P-T equals P-T', which is the distance from the point 74 to the intersection of needle 70 with gauge shaft 27. A confirming scan can be made to ensure that the thus-inserted needle 70 is on target.

If desired, screw threaded member 35 (similarly to nub 66 illustrated for needle holder 40 in FIG. 3) can be provided with a nub (not shown) at the end thereof which is adapted to mate securel albeit removably, with a connector 75 such that a circular angular indicator means 95 can be attached directly to member 35 to directly indicate the tilt angle of the turning plate 20.

In the embodiment of FIG. 1, the screw threaded height adjusting means comprises screws 3 and 5 which are positioned in the corresponding aperatures 2 and 4, respectively, in base 14, and screw 7 which is positioned in aperature 6 and which cooperates with thumb nut 8 (housed in a recessed slot (not shown) in base portion 16) to permit precise adjustment of the base height and level. If desired, an adhesive surface can be provided upon the bottom surface of each such screw 3, 5 and 7 to assist in stabilizing the device 10 on the surface of a patient's skin.

The foregoing description has been given for the purposes of understanding only, and it will be understood that no unnecessary limitations should be read therefrom, as some modifications will be apparent from the above description.

We claim:

1. A device for accurately positioning needles for percutaneous insertion through the skin of a patient to a predetermined target point in the patient's body which comprises: (i) a base, provided at one end thereof with a vertically disposed support member; (ii) turning plate means movably affixed to said base and adapted to be controllably tilted in a direction which is substantially parallel to the plane defined by said vertical support member; (iii) means for adjusting the tilt angle of said turning plate means; (iv) needle holding means, movably affixed to said turning plate means, for removably securing said needle therein and adapted to be tilted along said turning plate in a plane which is substantially perpendicular to the plane defined by said vertical support member; (v) means for adjusting the tilt angle of the needle holding means alog said turning plate means; and (vi) arcuate needle angle indicator means, attached to said turning plate means and provided with a plurality of spaced-apart radiopaque needle angle indicators, for providing a visible indication of said needle tilt angle along said turning plate means when the device is exposed to X-ray radiation, the balance of said device being constructed of a material which is substantially transparent or translucent to said radiation.

2. The device according to claim 1 wherein said needle holding means comprises a longitudinal grooved housing having a radiopaque linear line along the longitudinal axis thereof, and a clasp adapted to be removably secured on said housing and to hold said needle within said groove in a manner wich substantially avoids movement of said needle in a downward gravity direction.

3. The device according to claim 1 wherein said turning plate means and said needle holder are each adapted to be tilted through a total of from about 130 to about 170 degrees of arc in their respective planes of motion.

4. The device according to claim 1 which further comprises offset angle indicator means, including a circular angle indicator, adapted to be rotatably secured to said turning plate means such that the tilt angle of said turning plate means can be visually observed with respect to a focal point which is remote from said turning plate means, said offset angle indicator means having a tiltably adjustable linear shaft projecting uowardly from a base axis which corresponds to the axis defined by the plane of said turning plate means along the lower surface thereof, said circular angle indicator being rotatably affixed to the upper portion of said upwardly projecting shaft.

5. The device according to claim 1 wherein said needle holding means further comprises a circular angle indicator means having a shaft member adapted to move cooperatively with said needle holding means and having affixed to the upper portion of said shaft, a circular angular disk, rotatably affixed thereto, whereby the tilt angle of said needle holding means can be observed by reference to said circular disk.

6. The device according to claim 4 wherein said circular angle indicator is securely affixed to said upwardly projecting shaft and is provided with a rotatably secured, weighted pivoting angle indicator.

7. The device according to claim 5 wherein said circular angular disk is securely affixed to said shaft and is provided with a rotatably secured, weighted pivoting angle indicator.

* * * * *